United States Patent [19]
Crotty et al.

[11] Patent Number: 5,935,596
[45] Date of Patent: Aug. 10, 1999

[54] DELIVERY OF SKIN BENEFIT AGENTS VIA ADHESIVE STRIPS

[75] Inventors: Brian Andrew Crotty, Branford; Philip Edward Miner, Newtown; Anthony Johnson, Fairfield; Alexander Paul Znaiden, Trumbull; Joseph Michael Corey, Waterbury; Anthony Vargas, Monroe; Alan Joel Meyers, Trumbull, all of Conn.; Beth Anne Lange, Woodridge, N.J.

[73] Assignee: Chesebrough-Pond's USA Co., Greenwich, Conn.

[21] Appl. No.: 09/018,805

[22] Filed: Feb. 4, 1998

Related U.S. Application Data

[60] Provisional application No. 60/039,378, Mar. 20, 1997, and provisional application No. 60/072,355, Jan. 23, 1998.

[51] Int. Cl.$^6$ .................................................. A61K 9/70
[52] U.S. Cl. .................. 424/448; 424/401; 424/443; 424/444; 424/445; 424/446; 424/447; 424/449; 424/484; 514/458; 514/474; 514/844; 514/859
[58] Field of Search ........................ 424/401, 443, 424/444, 445, 446, 447, 448, 449, 484; 514/474, 458, 844, 859

[56] References Cited

U.S. PATENT DOCUMENTS

| | | | |
|---|---|---|---|
| 4,126,142 | 11/1978 | Saute | 132/7 |
| 4,752,472 | 6/1988 | Kligman | 424/81 |
| 4,762,124 | 8/1988 | Kerch et al. | 128/156 |
| 4,990,339 | 2/1991 | Scholl et al. | 424/443 |
| 5,026,552 | 6/1991 | Gueret et al. | 424/401 |
| 5,254,338 | 10/1993 | Sakai et al. | 424/78.35 |
| 5,466,456 | 11/1995 | Glover | 424/401 |
| 5,512,277 | 4/1996 | Uemura et al. | 424/78.03 |
| 5,605,694 | 2/1997 | Nadaud et al. | 424/401 |
| 5,723,138 | 3/1998 | Bae et al. | 424/401 |
| 5,736,128 | 4/1998 | Chaudhuri et al. | 424/78.03 |
| 5,811,107 | 9/1998 | Gangadharan et al. | |

FOREIGN PATENT DOCUMENTS

| | | |
|---|---|---|
| 206114 | 11/1959 | Austria . |
| 0 063 875 | 4/1982 | European Pat. Off. . |
| 0 309 309 | 3/1989 | European Pat. Off. . |
| 0 514 760 | 11/1992 | European Pat. Off. . |
| 2538247 | 6/1984 | France . |
| 2 734 574 | 5/1995 | France . |
| 55-127312 | 10/1980 | Japan . |
| 56-119499 | 7/1981 | Japan . |
| 56-120577 | 7/1981 | Japan . |
| 63-35511 | 2/1988 | Japan . |
| 63-57508 | 3/1988 | Japan . |
| 9-194325 | 7/1997 | Japan . |
| 2 144 133 | 2/1985 | United Kingdom . |
| 87/05206 | 9/1987 | WIPO . |
| 98/05283 | 2/1988 | WIPO . |
| 93/05893 | 4/1993 | WIPO . |
| 96/14822 | 5/1996 | WIPO . |
| 97/32567 | 9/1997 | WIPO . |

OTHER PUBLICATIONS

"Proposing New Lifestyles. Superiior Product Creation: Biore Pore Back"—available from Internet: URL:HTTP://WWW.KAO.CO.JP/AR97/PE.HTM, 1997, XP002072734.

"Les maasques de beaute" by A. Julien et al., *Parfums, Cosmetiques, aromes*, No. 72, Dec. 1986.

Translation of KAO Biore Package (Japan)—1997.

*Primary Examiner*—Thurman K. Page
*Assistant Examiner*—Lakshmi Channavajjala
*Attorney, Agent, or Firm*—Milton L. Honig

[57] ABSTRACT

A cosmetic product is provided for delivery of skin actives through adhesive strips which concurrently remove keratotic plugs from skin pores. The product is a strip including a flexible substrate sheet onto which a composition containing an adhesive polymer is deposited. The composition is essentially a polymer of anionic, cationic, nonionic, amphoteric or zwitterionic variety which increases in tackiness upon being wetted, with wetting occurring just prior to application onto the skin thereby enhancing the composition's adhesivity. Skin agents delivered through the adhesive strip include vitamins, herbal extracts, alpha- and beta-hydroxycarboxylic acids, ceramides, anti-inflammatories, antimicrobials, vasoconstrictors, zinc salts and mixtures thereof. The strips are sealably enclosed within a pouch for purposes of moisture protection.

7 Claims, No Drawings

DELIVERY OF SKIN BENEFIT AGENTS VIA ADHESIVE STRIPS

This application is a provision of Ser. No. 60,/039,378 filed Mar. 20, 1997, and a provision of Ser. No. 60/072,355 filed Jan. 23, 1998.

BACKGROUND OF THE INVENTION

1. Field of the Invention

The invention concerns adhesive strips applied to the skin for removing keratotic plugs from pores and concurrent delivery of skin benefit agents.

2. The Related Art

A variety of vehicles exist for delivery of actives to the skin. These vehicles may be lotions, creams, pads, sprays and even masks. Some are leave-on systems while others are intended as short-lived wash-off products. Those who practice cosmetic arts know the critical role that vehicles perform in delivering actives effectively to skin.

Delivery is not the only concern. Some types of actives are degraded by the vehicle. For instance, ascorbic acid, also known by its common name of Vitamin C, is a very unstable substance. Although readily soluble in water, rapid oxidation occurs in aqueous media. Solubility of ascorbic acid has been reported to be relatively poor in nonaqueous media, thereby preventing an anhydrous system from achieving a significant level of active concentration. Derivatives have been produced with greater stability than the parent component. See U.S. Pat. No. 5,137,723 (Yamamoto et al.) and U.S. Pat. No. 5,078,989 (Ando et al.). A two-pack approach has been developed where Vitamin C powder and other ingredients are separately packaged in different containers with mixing just prior to use. See U.S. Pat. No. 4,818,521 (Tamabuchi). Water compatible alcohols such as propylene glycol, polypropylene glycol and glycerol have been used as co-carriers alongside water to improve stability. See U.S. Pat. No. 4,983,382 (Wilmott and Znaiden).

Vitamin C is just one example of difficult to formulate cosmetic ingredients. Many other types of vitamins, herbal extracts and alpha- or beta-hydroxycarboxylic acids have one or more properties which render them sensitive to certain types of delivery vehicles.

Masks have been employed to deliver herbal extracts to the face. Among the extracts have been glycyrrhizinic acid, α-bisabolol, azulene, yarrow, coltsfoot, sage, myrrh, rosemary and others. See U.S. Pat. No. 5,614,201 and U.S. Pat. No. 5,482,710, both to Slavtcheff et al. These mask products are reported to eliminate pimples, blemishes and the redness of acne. Unfortunately delivery via masks requires the presence of significant amounts of water which may adversely react with moisture sensitive ingredients. Extended drying times are also necessary for evaporation of water from the applied mask material. Finally, masks have relatively low adhesivity. These products are insufficiently sticky to effect "rip-off" of pore plugs and accumulated dead skin cells which otherwise would be barriers or at least hindrances to the penetration of the cosmetic actives.

Within the last two years, cleansing pore strips have entered commerce in a number of countries. Products such as Kao Biore® and Pond's® Cleansing Pore Strips are sheets of an adhesive coated flexible band-aid shaped strip which when wetted have sufficient adhesivity to remove keratotic plugs from skin pores. The strips are left on the skin for approximately 15–30 minutes to allow adhesive polymer to penetrate the pores. Removal of the strip rips away the plugs as well as a layer of skin. These products do not contain any skin benefit agents. In fact, the whole concept behind the strips is removal rather than deposition.

It is an object of the present invention to provide a delivery system for vitamins, herbal extracts and hydroxycarboxylic acids which assists penetration of these actives into the human skin.

Another object of the present invention is to provide a delivery system for vitamins, herbal extracts and hydroxycarboxylic acids which does not interfere or degrade the active during storage.

These and other objects of the present invention will become more readily apparent through the following summary, detailed discussion and examples.

SUMMARY OF THE INVENTION

A cosmetic product for delivery of skin actives is provided which includes:

(A) a strip including:
  (i) a flexible substrate sheet; and
  (ii) a composition containing a polymer selected from the group consisting of anionic, cationic, nonionic, amphoteric, zwitterionic and polymer mixtures thereof deposited onto the substrate sheet, the composition further including an active selected from the group consisting of vitamins, herbal extracts, alpha- and beta-hydroxycarboxylic acids, ceramides, anti-inflammatories, antimicrobials, vasoconstrictors, zinc salts and mixtures thereof; the composition increasing in tackiness upon being wetted just prior to use thereby enhancing the composition adhesivity to skin; and
(B) a pouch sealably enclosing the strip.

DETAILED DESCRIPTION OF THE INVENTION

Now it has been discovered that adhesive strips designed to remove keratotic plugs are exceptional vehicles for the delivery of active ingredients into the skin. Actives covered by the present invention are vitamins, herbal extracts, alpha- and beta-$C_1$–$C_{30}$ hydroxycarboxylic acids, ceramides, anti-inflammatories, anti-microbials, vasoconstrictors, zinc salts and mixtures thereof.

Vitamins covered by the present invention include Vitamin A, Vitamin B, Vitamin C, Vitamin E and combinations thereof. Most preferred is Vitamin C which not only is defined as including ascorbic acid but also salts and esters thereof such as magnesium ascorbyl phosphate, ascorbyl palmitate, L-ascorbyl stearate, dehydroascorbic acid, Vitazyme C and combinations thereof. Adhesive carriers of the present invention are particularly useful for Vitamin C delivery because it is very unstable in the presence of water yet relatively poorly soluble in non-aqueous media. These problems are overcome in the present carrier system where during manufacture Vitamin C contacts an aqueous media for only a short period of time to allow transfer onto a flexible substrate. Almost all the water is removed immediately thereafter. The final product may contain less than 20% water, but usually less than 10%, optimally less than 7% water.

Vitamin A for purposes of this invention will include retinol, retinoic acid as well as retinyl $C_2$–$C_{22}$ fatty acid esters. Most preferred among the esters are retinyl palmitate and retinyl linoleate. Vitamin E may be provided in the form of tocotrienols, α-tocopherol, β-tocopherol, γ-tocopherol and δ-tocopherol. Included within the Vitamin E group are tocopheryl $C_2$–$C_{22}$ fatty acid esters including tocopheryl acetate, tocopherol linoleate and tocopheryl palmitate. Vitamin B may be present in the form of thiamine, riboflavin, niacin, pantothenic acid, biotin, cobalamin, pyridoxine hydrochloric, pyridoxamine dihydrochloride, pyridoxal, pyridoxal phosphate, folic acid, inositol and mixtures as well as complexes thereof. Under the term vitamin may also be included thaproline, L-caritine, nicotinic acid, nicotinamide and cyproterone acetate.

Herbal extracts particularly suitable for the present invention are antioxidants or free-radical inhibitors. Examples of these extracts include:

| PLANT/EXTRACTS | SOLUBILITY (W = WATER, O = OIL) |
|---|---|
| basil leaf | O and w |
| bell pepper | o and w |
| black tea extracts | w |
| blackberry | w |
| black currant fruit | w |
| chamomile | o |
| carrot root | o |
| coffee seed | w |
| dandelion root | o and w |
| date palm fruit | o and w |
| echinacea purpurea | o |
| fennel | o |
| gingko leaf | w |
| ginseng | o |
| grape seed | o |
| grape skin | o |
| grapefruit | o |
| green tea polyphenyls (i.e. including epicatechin gallate and epigallocaatechin 3-O-gallate) | w |
| guggalipids | o |
| harpogophytum | o |
| hawthorn berries | w |
| jasmine | o |
| licorice | w and o |
| marjoram | o |
| myrrh gum resin | o |
| onion | o |
| pine bark | o |
| red clover flower | o |
| resveratrol | o |
| rosemary | o |
| sage | w |
| sesame | o |
| St. Johns wort | o |
| strawberry | w |
| sweet pea | w |
| tomato | o and w |
| thyme | o |
| Uva Ursi (bearberry) | o |
| vanilla fruit | w |
| borage seed oil | o |
| wild borage seed oil | o |
| Flavanoid Extracts | |
| hesperedin | o |
| neohesperidin | w |
| quercetin | o |
| rutin | w |
| morin | w |
| kaempherol | o |
| myricetin | w/o |
| genistein | o |
| Phytoestrogen Extracts | |
| coumestrol | o |
| estriol | o |
| phytosterols | o |
| Other Extracts | |
| limonene | o |
| ethoxyquin | o |
| chlorogenic acid | w |
| glutathione | w |
| hydroquinone | o |
| ubiquinone (coenzyme Q) | o |
| lipoic acid | o |
| N-acetyl cysteine | o |
| curcumin | o |

Herbal extracts particularly effective for sebum/oil control include dill, horseradish, oats, neem, beet, broccoli, tea, pumpkin, soybean, barley, walnut, flax, ginseng, poppy, avocado, pea, sesame, dandelion, wheat, nettle, cashew, pineapple, apple, asparagus, Brazilnut, chickpea, grapefruit, orange, cucumber, buckwheat, strawberry, ginko, tomato, blueberry, cowpea and grape extracts.

Other herbal extracts also suitable are those of ivy horse chestnut, centella asiatica, rosmarinic acid, glycyrrizinate derivatives, alpha bisabolol, azulene and derivatives thereof, asiaticoside, sericoside, ruscogenin, escin, escolin, betulinic acid and derivatives thereof, catechin and derivatives thereof.

Alpha- and beta-hydroxycarboxylic acids ranging from $C_2$–$C_{30}$ are also suitably delivered by the adhesive strips of the present invention. The beta-hydroxycarboxylic acids are primarily exemplified by salicylic acid and $C_1$-$C_{30}$ ester and salt derivatives. Examples of suitable alpha-hydroxycarboxylic acids include but are not limited to:
alpha hydroxy acetic acid (glycolic acid)
alpha hydroxybenzeneacetic acid (mandelic acid)
alpha hydroxypropionic acid (lactic acid)
alpha hydroxybutanoic acid
alpha hydroxyhexanoic acid
alpha hydroxyoctanoic acid (alpha hydroxycaprylic acid)
alpha hydroxynonanoic acid
alpha hydroxydecanoic acid
alpha hydroxyundecanoic acid
alpha hydroxydodecanoic acid (alpha hydroxylauric acid)
alpha hydroxytetradecanoic acid
alpha hydrocyhexadecanoic acid
alpha hydroxyoctadecanoic acid
alpha hydroxyoctaeicosanoic acid;
dicarboxylic alpha hydroxy acids;
dihydroxybutanedioic acid (tartaric acid)
2-hydroxybutanedioic acid (malic acid)
2-hydroxy propanedioic acid
2-hydroxy hexanedioic acid
2-hydroxy octanedioic acid
2-hydroxy decanedioic acid
2-hydroxy dodecanedioic acid
2-hydroxy myristicdioic acid
2-hydroxy palmiticdioic acid
Tricarboxylic alpha hydroxy acid;
2-hydroxy-1,2,3,-propanetricarboxylic acid (citric acid)
1-hydroxy-1,2,3-propanetricarboxylic acid (isocitric acid) and mixtures thereof.

$C_1$–$C_{30}$ esters and salts of alpha- and beta-hydroxycarboxylic acids (e.g. potassium, sodium, ammonium, triethanolammonium salts) are also meant to be included within the term "alpha- and beta-hydroxycarboxylic acid". Depending on the pH of the composition, a mixture of the salt and the acid may be present.

The preferred alpha hydroxycarboxylic acids are monocarboxylic acids, in order to improve skin penetration and efficacy.

Even more preferably, the hydroxy acid is chosen from lactic acid, glycolic acid, mandelic acid, and mixtures thereof to optimize the efficacy of compositions by increasing percutaneous absorption. Most preferred is the L-form of an alpha hydroxycarboxylic acid.

Ceramides useful for the present invention are sphingolipids or phytosphingolipids including Ceramide 1, Ceramide 3 and Ceramide 6.

Anti-inflammatories of the present invention are illustrated by corticoids such as beta-methasone 17-acetate, indomethacin, ketoprofen, flufenamic acid, ibuprofen, diclofenace, diflunisal, fenclofenac, naproxen, piroxidam and sulindac. Antimicrobials illustrative of the present invention include, chlorohexidine, hexetidine, 3,4,4'-trichlorocarbanilide, (tricarbanilide) 2,4,4'-trichloro-2-hydroxydiphenyl ether (triclosan), cetyl pyridinium chloride, benzalkonium chloride, $C_2$–$C_{20}$ organoperoxy compounds (e.g. benzoyl peroxide) and mixtures. Vasoconstrictors are illustrated by compounds such as papaverine, yohimbine, visnadin, khellin, bebellin and nicotinate derivatives. Zinc salts which may be effective include zinc thaproline, zinc chloride, zinc sulfate, zinc phenolsulfonate and zinc pyrithione. Other substances within one or more of the above categories of actives include resorcinol, azelaic acid, oxamic acid and cyoctol.

Actives of the present invention may range from 0.00001 to 40%, preferably from 0.01 to 20%, optimally from 0.1 to 10% and in some instances from 1 to 8% by weight of the composition. Of course, vitamins and herbal extracts are usually employed at much lower levels than for instance the hydroxycarboxylic acids. Thus, vitamins may range from 0.0001 to 1%, preferably from 0.001 to 0.5% by weight for Vitamin A, Vitamin B and Vitamin E. Much higher levels may be tolerated for Vitamin C and these may range preferably from 0.01 to 40%, optimally from 0.1 to 30% by weight.

Preferably the amount of the hydroxycarboxylic acid component present in the composition according to the invention is from 0.5% to 20%, more preferably from 1% to 15%, and most preferably from 3.0% to 12.0% by weight of the composition.

Actives of the present invention will be formulated onto a flexible substrate sheet impregnated with an adhesive composition containing an anionic, cationic, nonionic, amphoteric or zwitterionic polymer. In a dry state, the composition preferably but not necessarily is non-tacky to the touch. The impregnated substrate sheet is sealably enclosed in a pouch, particularly a laminated foil package to control moisture level.

Pouches of the present invention are normally of the laminated foil variety. These are heat sealed and utilize foils with very low vapor (e.g. moisture) transmission rates (a rate of transmission less than 5% per day, preferably less than 1% per day volatile fluid gain or loss). Walls suitable for the pouch may utilize polyester, polyethylene or polypropylene sheets, several layers of which can be laminated together. These layers may also be provided with a coating of wax or other volatile fluid impermeable material.

The product is used by removing the strip from its usually individually wrapped pouch and either directly wetting the composition on the sheet or indirectly by wetting the face in areas to be contacted by the composition. In either instance, the wetting agent interacts with the composition so it becomes tacky and sufficiently mobile to flow into skin pores. The time between removal of strip from the pouch and use may be anywhere from 5 seconds to several hours, usually from 10 to 20 seconds. Pure water is the preferred wetting agent. However, other liquid systems or gels could be employed. Suitable wetting agents would include alcohols such as ethanol, propanol, propylene glycol, polyethylene glycol, polypropylene glycol and especially mixtures of these alcohols with water. Gels would normally consist of structured liquids (particularly water) thickened with structuring agents such as Carbomer.

Subsequent to wetting, the composition is allowed to dry over the area of treatment. During drying the keratotic plugs stickingly adhere to the composition. Advantageously the drying period ranges from 1 minute to 5 hours, preferably from 5 minutes to 1 hour, optimally from 10 to 20 minutes. Thereafter, the dried composition with adhered plugs is peeled from the skin.

Mobility of the composition may be measured by yield point. The yield point should range from 1 to 400 Pascals, preferably from 20 to 200, optimally from 50 to 100 Pascals.

The composition will include an adhesive polymer which may either be anionic, cationic, nonionic, amphoteric, zwitterionic or mixtures thereof. Mixtures may be of polymers within any one category or between different category types. Illustrative of the latter, and a preferred embodiment, is a combination of an anionic and nonionic polymer.

Examples of nonionic polymers suitable for adhesive film deposition are the copolymers of vinyl acetate and crotonic acid, terpolymers of vinyl acetate, crotonic acid and a vinyl ester of an alpha-branched saturated aliphatic monocarboxylic acid such as vinyl neodecanoate; copolymers of methyl vinyl ether and maleic anhydride (molar ratio about 1.1) wherein such copolymers are 50% esterified with a saturated alcohol containing from 1 to 4 carbon atoms such as ethanol or butanol; and acrylic copolymers, terpolymers, etc., containing acrylic acid or methacrylic acid esters of acrylic or methacrylic acid with one or more saturated alcohols having from 1 to 22 carbon atoms such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate, glycols having from 1 to 6 carbon atoms such as hydroxypropyl methacrylate and hydroxyethyl acrylate, styrene, vinyl caprolactam, vinyl acetate, acrylamide, alkyl acrylamides and methacrylamides having 1 to 8 carbon atoms in the alkyl group such as methacrylamide, t-butyl acrylamide and n-octyl acrylamide, and other compatible unsaturated monomers. One specific example is the emulsion polymerized terpolymer of methacrylic acid, n-butyl acrylate and ethyl acrylate (e.g., in a weight percent ratio of 31:42:27, respectively).

Further examples of nonionic adhesive polymers are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 under the trademark PVP K-90 and those having an average molecular weight of about 1,000,000 sold under the trademark of PVP K-120. Particularly preferred is poly(methyl vinyl ether/maleic anhydride) as an unneutralized resin available from ISP Corporation under the trademark Gantrez® S-97 BF.

Anionic adhesive polymers often are derived from the nonionic types which include carboxylic acid functions.

Alkaline agents are employed to neutralize the carboxylic acid or anhydride transforming them into anionic salts. Examples of suitable neutralizing agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). Most preferred is AMP.

Particularly preferred anionic polymers are the salts of poly(methyl vinyl ether/maleic anhydride) and polystyrene sulfonic acid. The former is obtained by at least partial neutralization of Gantrez® S-97 BF and the latter available from the National Starch & Chemical Company under the trademarks Versa TL-501 and Flexan® 130 having respective molecular weights of about 500,000 and 100,000. Other polymer films which may be employed and are commercially available as listed in the Table below.

TABLE I

| POLYMER TRADEMARKS (SUPPLIER) | CTFA DESIGNATIONS |
|---|---|
| Resyn ® 28-1310 (NSC) | Vinyl acetate/crotonic acid copolymer |
| Resyn ® 28-2930 (NSC) | Vinyl acetate/crotonic acid/vinyl neodecanoate copolymer |
| Resyn ® 28-2913 (NSC) | Vinyl acetate/crotonic acid/vinyl neodecanoate copolymer |
| Versatyl ® 40 (NSC) | Octylacrylamide/acrylates copolymer |
| Versatyl ® 42 (NSC) | Octylacrylamide/acrylates copolymer |
| Experimental Resin (NSC) | Vinyl acetate/vinyl neodecanoate/maleic half-ester |
| Ultrahold-8 ® (BASF) | Acrylate/acrylamide copolymer |
| Luviset ® CAP (BASF) | Vinyl acetate/crotonic acid/vinyl propionate copolymer |
| PVP K-30 (ISP) | PVP |
| PVP/VA E-335 (ISP) | PVP/Vinyl acetate copolymer |
| PVP/VA E-735 (ISP) | PVP/Vinyl acetate copolymer |
| Gantrez ® ES-225 (ISP) | Ethyl ester of PVM/MA copolymer |
| Gantrez ® ES-425 (ISP) | Butyl ester of PVM/MA copolymer |
| Gaffix ® VC-713 (ISP) | Vinyl caprolactam/PVP/dimethyl aminoethyl methacrylate copolymer |

Cationic adhesive polymers suitable for the present invention may be prepared as homo- or copolymers from monomers including:

Dimethyl aminoethyl acrylate (DMAEA), Dimethylaminoethyl methacrylate (DMAEMA), Dimethylaminopropylacrylamide (DMAPAAm), and Dimethylaminopropyl methacrylamide (DMAPMAAm) which are all (meth)acrylamides or (meth)acrylic acid esters having a dialkylamino group;

Dimethylaminostyrene (DMASt) and Dimethyaminomethylstyrene (DMAMSt) and the like which are styrenes having a dialkylamino group;

4-Vinyl pyridine and 2-vinyl pyridine which are vinyl pyridines; and

Quaternized products of these with a known quaternizing agent such as alkyl halide, benzyl halide, alkyl or aryl sulfonic acid, or dialkyl sulfate.

Among suitable amphoteric adhesive polymers are those derived from monomers such as:

N-(3-sulfopropyl)-N-acryloyloxyethyl-N,N-dimethylammonium betaine, N-(3-sulfopropyl)-N-methacrylamidepropyl-N,N-dimethylammonium betaine, N-(3-carboxymethyl)-N-methacroylamidepropyl-N,N-dimethylammonium betaine and N-carboxymethyl-N-methacroyloxyethyl-N,N-dimethylammonium betaine.

When the salt forming group of the cationic and amphoteric polymers is not ionized, it is preferred to ionize it via neutralization with known acids such as hydrochloric acid and sulfuric acid which are inorganic acids; acetic acid, propionic acid, lactic acid, succinic acid, glycol acid which are organic acids, or with known bases such as triethylamine, trimethylamine which are tertiary amines; ammonia; or sodium hydroxide.

Most polymers suitable for the present invention will be relatively brittle when dried. Therefore, they require a supporting surface which is a flexible substrate sheet. Substrate sheets of the present invention may either be occlusive or non-occlusive. Preferably but not necessarily the sheets are non-occlusive to allow water evaporation from the deposited polymer as the film maturates. Non-occlusivity or breathability is achieved either through use of a hydrophobic substrate having physical porosity (e.g. pore channels) or a hydrophilic substrate wherein the material of construction inherently allows for breathability. Suitable materials include cellulosics such as rayon, wool, cotton, linen, thermoplastic fibers and combinations thereof. They may be woven or nonwoven. Nonwoven rayon is a preferred substrate. Materials formed from combinations of cellulosic with thermoplastic fibers may also be employed. For instance, a hydrophilic polypropylene/rayon combination can be employed for the present invention.

It is advantageous to employ a ratio of composition to substrate sheet in amount ranging from 0.1:1 to 1,000:1, preferably 0.5:1 to 100:1 and optimally 0.8:1 to 10:1 by weight. The polymer ordinarily will constitute from 50 to 100%, preferably from 75 to 99%, optimally from 85 to 95% by weight of the composition deposited onto the substrate sheet.

Minor adjunct ingredients may also be included such as fragrances, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A variety of polymers were evaluated for their adhesive effects in removing keratotic plugs from the skin. The polymers listed in Table II below were coated onto a non-woven resin bonded rayon (1 ounce/square yard). A knife-over-roll was utilized in the coating operation. After coating, the non-woven polymer impregnated substrate sheets were dried at 75° C. in a convection oven. They were then cut into small patches.

The test patches were applied to the face of panelists in an area containing several plugged pores. The plugged pores were counted. Water was applied to the patch and it was then placed over the test area with wet side down. Next, the patch was allowed to dry whereupon it was peeled off. The number of plugs removed were counted as they appeared on the adhesive patch. Percentage of plugs removed were calculated to reflect efficiency of the test product.

TABLE II

| POLYMER | % DRIED POLYMER ON NON-WOVEN | % PLUGS REMOVED |
|---|---|---|
| Dextrine | 409 | 5–15 |
| Polyvinyl Alcohol | 441 | 10–20 |
| Polyvinyl Acetate | 347 | 30–40 |
| Polyacrylamidomethylpropane Sulfonic Acid | 119 | 5–15 |

TABLE II-continued

| POLYMER | % DRIED POLYMER ON NON-WOVEN | % PLUGS REMOVED |
|---|---|---|
| Polyacrylamidomethylpropane Sulfonic Acid | 275 | 25 |
| Poly(methyl vinyl ether/maleic anhydride) | 113 | 90–100 |
| 98% Poly(methyl vinyl ether/maleic anhydride) + 2% 2-amino-2-methyl-1-propanol | 116 | 80–95 |
| 90% Poly(methyl vinyl ether/maleic anhydride) 10% Polyacrylamido methylpropane Sulfonic Acid | 145 | 90–100 |

EXAMPLE 2

Poly(Methyl Vinyl Ether Maleic Anhydride) Gantrez S-97 BF was coated by knife-over-roll (25 mil.) over various nonwoven materials. After coating, the nonwoven materials were dried at 75° C. in a convection oven and then cut into small patches. The test procedure was similar to that reported under Example 1. Results are reported in Table III.

TABLE III

| NONWOVEN | % PLUGS PULLED | OBSERVATIONS |
|---|---|---|
| PGI 5255 Rayon Resin bonded (1 oz./sq.yard) | 90–100 | Nice appearance |
| Veratec 9408810 Polyester/cellulose Wet laid (1.2 oz/sq. yard) | 70–100 | Nice appearance: Nonwoven may be too weak |
| Veratec 2006094 Polypropylene Thermal Bond (.6 oz/sq. yard) | 40–60 | Nice appearance |
| Veratec Polyethylene (.5 oz/sq. yard) | 10 | Poor appearance: When used in application adhesive dried very slow. |

EXAMPLE 3

The following experiments were conducted to demonstrate the efficacy of employing adhesive strips activated just prior to use by water in the delivery of skin benefiting agents. More particularly, the experiments reported herein concerned delivery of Vitamin C for anti-oxidant benefits.

Lipid Peroxidation Test For Anti-Oxidant Activity

A vulnerable target for free radicals in facial skin is the lipids. Lipid peroxidation can lead to membrane fluidity changes, altered activity of membrane-bound enzymes and receptors, changes in ion permeability, protein and DNA damage and mutagenesis, which may contribute to atrributes of unhealthy skin. Lipid peroxidation can be induced in skin by UV radiation, ozone, environmental pollutants and other stresses. Although not wishing to be bound by any theory, initiation of peroxidation is believed to involve the abstraction of a hydrogen atom from the methylene carbon located between two adjacent double bonds in a polyunsaturated fatty acid, resulting in the formation of a lipid radical, L. In the membrane bilayer, oxygen reacts with this lipid-free radical to generate a lipid peroxyl radical, LOO. This reaction is rapid, approaching the theoretical diffusion rate. The lipid peroxyl radical can then propagate the formation of other lipid radicals, while itself generating a lipid hydroperoxide, LOOH.

Procedure And Results

The study involved four panelists. An adhesive strip of approximate size 1×3 inches having Gantrez S-97 BF® as described under Example 2 was coated onto PGI 5255 rayon sheet and cut into half. A first of the halves was employed as a blank or control strip. The other half was impregnated with an aqueous solution of ascorbic acid and then immediately dried in an oven to achieve a non-tacky strip. This half of the original strip was wetted in conjunction with a blank, to regenerate tackiness. Both halves were then applied to the forehead of each panelist. Application on the forehead was for a period of 15 minutes.

After removal of the control and additive containing strips, a Sebutape sample was taken from each site at 30 minutes, 1 hour and 3 hours. In all experiments, sebum was collected using Instant Sebutapes (CuDerm Corporation, Dallas, Tex., 1 cm$^2$ sampling area) held on the panelist's forehead with even pressure for 15 seconds.

Plastic sampling areas were peeled away from cardboard backing. The Sebutape was then treated with 100 $\mu$l of isopropanol in a test tube. The test tube was vortexed until the Sebutape was saturated. It was then analyzed for lipid hydroperoxide content using the K-Assay LPO-CC assay kit (Kamiya Biochemical Company, Seattle, Wash.). The assay measures lipid hydroxyperoxides as follows: In the presence of hemoglobin, lipid hydroperoxides are reduced to hydroxyl derivatives (lipid alcohols) and the 10-N-Methylcarbamoyl-3,7-dimethylamino-10H-phenothiazine (MCDP) chromagen is oxidatively cleaved to form methylene blue in an equal molar reaction. Lipid peroxides are then quantitated colorimetrically measuring the methylene blue at 675 nm (Kamiya Biochemical Company, assay protocol). LPO values are calculated according to the following equation:

$$LPO \text{ (nmol/ml)} = \frac{\text{(Absorbance SAMPLE} - \text{Absorbance BLANK)}}{\text{(Absorbance STANDARD} - \text{Absorbance BLANK)}} \times 50$$

Results of the test are recorded under Table IV.

TABLE IV

| PANELIST | 30 MINUTES POST | | 1 HOUR POST | | 3 HOUR POST | |
|---|---|---|---|---|---|---|
| | BLANK | 3% ASCORBATE | BLANK | 3% ASCORBATE | BLANK | ASCORBATE |
| 1 | 72 | 98.4 | 47.9 | 68.9 | 90.4 | 69.3 |
| 2 | 39.2 | 70.4 | 54.3 | 43.1 | 139.5 | 202.6 |
| | BLANK | 6% ASCORBATE | BLANK | 6% ASCORBATE | BLANK | 6% ASCORBATE |
| 3 | 24 | 32 | 18.1 | 25 | 29.8 | 23.7 |
| 4 | 39.2 | 52.8 | 75.9 | 44.8 | 315.8 | 109.6 |

In the 30 minute sample, all of the four panelists had lower lipid hydroxyperoxide values on the control strip than on the ascorbate treated side. This result is believed to occur because the control adhered better than the ascorbate containing strips, thus pulling more lipids from the skin. In the one hour sample, two of the four panelists on their ascorbate treated sides were found to have lower levels of lipid hydroperoxide than the control (blank) side. Moreover, all of the ascorbate treated site values were lower than their original 30 minute readings. After three hours, three out of the four panelists on their ascorbate treated sides exhibited lower lipid hydroperoxide values than the control side. It is evident that over a period of time, the ascorbate was highly effective in its anti-oxidant performance against the skin.

The foregoing description and examples illustrate selected embodiments of the present invention. In light thereof variations and modifications will be suggested to one skilled in the art, all of which are within the spirit and purview of this invention.

What is claimed is:

1. A cosmetic product for delivery of skin actives comprising:
    (A) a strip comprising:
        (i) a flexible substrate sheet; and
        (ii) a dry composition deposited onto said substrate sheet, the composition containing from 75 to 99% of a poly(methyl vinyl ether/maleic anhydride) copolymer and an active selected from the group consisting of vitamins, herbal extracts, alpha- and beta-hydroxycarboxylic acids, ceramides, anti-inflammatories. antimicrobials, vasoconstrictors, zinc salts and mixtures thereof; the composition increasing in tackiness upon being wefted just prior to use thereby enhancing the composition adhesivity to skin; and
    (B) a pouch sealably enclosing the strip.

2. The product according to claim 1 wherein the vitamins selected from the group consisting of Vitamin A, Vitamin B, Vitamin C, Vitamin E and combinations thereof.

3. The product according to claim 2 wherein the Vitamin C is selected from the group consisting of ascorbic acid, magnesium ascorbyl phosphate, ascorbyl palmitate, L-ascorbyl stearate dehydroascorbic acid and combinations thereof.

4. The product according to claim 1 wherein the amount of active ranges from 0.00001 to 40% by weight.

5. The product according to claim 1 wherein the sheet is rayon.

6. The product according to claim 1 wherein the deposited polymer and substrate sheet are present in a weight ratio ranging from 0.1:1 to 1,000:1.

7. The product according to claim 1 wherein the amount of polymer ranges from 85 to 95% by weight of composition deposited onto the substrate sheet.

* * * * *

UNITED STATES PATENT AND TRADEMARK OFFICE
CERTIFICATE OF CORRECTION

PATENT NO. : 5,935,596
DATED : August 10, 1999
INVENTOR(S) : Crotty et al.

It is certified that error appears in the above-indentified patent and that said Letters Patent is hereby corrected as shown below:

Column 1, line 63, delete "band-aid shaped".

Signed and Sealed this

Twenty-ninth Day of February, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO. : 5,935,596
DATED : August 10, 1999
INVENTOR(S) : Crotty et al.

It is certified that error appears in the above-indentified patent and that said Letters Patent is hereby corrected as shown below:

On the Title page, item [73]

Assignee Section, change "Chesebrough-Pond's USA Co.," to

-- Chesebrough-Pond's USA Co., Division of Conopco, Inc. -- ; and

Column 12, line 22, change "wefted" to -- wetted -- .

Signed and Sealed this

Twenty-ninth Day of August, 2000

Attest:

Q. TODD DICKINSON

*Attesting Officer*  *Director of Patents and Trademarks*